United States Patent [19]

Theeuwes et al.

[11] 4,455,143
[45] Jun. 19, 1984

[54] OSMOTIC DEVICE FOR DISPENSING TWO DIFFERENT MEDICATIONS

[75] Inventors: Felix Theeuwes, Los Altos; Brian Barclay, Menlo Park; Richard Cortese, San Jose, all of Calif.

[73] Assignee: ALZA Corporation, Palo Alto, Calif.

[21] Appl. No.: 360,396

[22] Filed: Mar. 22, 1982

[51] Int. Cl.³ .......................................... A61M 31/00
[52] U.S. Cl. ................................................. 604/890
[58] Field of Search ............................ 604/890–900; 424/19–25

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,111,202 | 9/1978 | Theeuwes | 128/260 |
| 4,210,139 | 7/1980 | Higuchi | 128/260 |
| 4,298,003 | 11/1981 | Theeuwes et al. | 128/260 |

*Primary Examiner*—Benjamin R. Padgett
*Assistant Examiner*—T. J. Wallen

*Attorney, Agent, or Firm*—Paul L. Sabatine; Edward L. Mandell; Steven F. Stone

[57] ABSTRACT

An osmotic device is disclosed for delivering two beneficial drugs to an environment of use. The device comprises a semipermeable wall surrounding a lumen divided into a first compartment containing a drug that is separated from a second compartment containing a different drug. An orifice through the wall communicates with the first compartment for delivering drug from the first compartment, and another orifice through the wall communicates with the second compartment for delivering drug from the second compartment. In operation, drug is dispensed separately from each compartment by fluid being imbibed through the wall into each compartment at a rate controlled by the permeability of the wall and the osmotic pressure gradient across the wall against the drug in each compartment thereby producing in each compartment a solution containing drug that is dispensed through their orifices at a controlled and continuous rate over a prolonged period of time.

38 Claims, 8 Drawing Figures

OSMOTIC DEVICE FOR DISPENSING TWO DIFFERENT MEDICATIONS

FIELD OF THE INVENTION

This invention pertains to an osmotic system manufactured in the form of an osmotic device. More particularly, the invention relates to an osmotic device that houses separately and dispenses separately at least two different drugs for (a) obtaining the therapeutic benefits of each drug, or for (b) lessening the incidence of adverse effects due to the incompatibility of different drugs.

BACKGROUND OF THE INVENTION

It is frequently desirable to prescribe pharmaceutical dosage forms containing at least two different drugs for obtaining the pharmacological benefits of each drug. The coadministration of certain drugs is prescribed often in fixed ratios for several reasons. For example, for drugs that have the same therapeutic effect but act mechanistically different on the body, such combinations may have the added therapeutic effect of both agents but less side effects, or the drugs may act synergistically and create a larger than additive effect. Also, drug combinations are prescribed for treatments where each individual drug address different symptoms of a particular medical situation. Although, a large number of therapeutic combinations could be provided, often they can not be compounded in the same dosage form because each drug needs to be administered on a different schedule. The different schedule is needed because different biological half lives and therapeutic indices, and therefore each drug should be administered in separate dosage forms on a prescribed schedule that is specific for each drug. Thus, a drug that needs to be administered four times a day, should not be combined with a drug that should be administered once a day. These drugs are kinetically incompatible in a pharmaceutical dosage form. Another reason why certain drugs cannot be combined is they may be chemically incompatible or unstable in the presence of each other. This kinetic or chemical incompatibility can be eliminated by the novel dosage form provided by this invention. For example, by using the dosage form provided by this invention, a regimen consisting of four times a day administration of drug can be transformed into a once a day administration such that the drug previously administered four times daily can be combined with a drug administered once daily. In other words, both drugs can be coadministered to the body at delivery rates that are matched to achieve each of their separate therapeutic plasma combinations. Thus, in the light of the above presentation, it will be appreciated by those versed in the dispensing art, that if a delivery device is made available for housing two or more different drugs at controlled and continuous rates in therapeutically effective amounts for obtaining the benefits of each drug, such a delivery device would have a definite use and be a valuable contribution to the dispensing art.

OBJECTS OF THE INVENTION

Accordingly, it is an immediate object of this invention to provide an osmotic device that contributes to the prior art by making available an osmotic device that can dispense at least two different beneficial drugs over a prolonged period of time for obtaining the pharmacological and the physiological benefits of each drug.

Another object of this invention is to provide a dosage form for separately housing and separately dispensing at least two drugs and which dosage form overcomes the problems known to the prior art.

Yet another object of the invention is to provide an osmotic device that provides independent controlled and continuous delivery of two drugs to biological drug receptors over a prolonged period of time.

Yet another object of the invention is to provide an osmotic device that can dispense separately two different drugs at controlled and continuous rates for performing their intended therapeutic effects.

Still a further object of the invention is to provide an osmotic device that can administer independently two different drugs as a complete pharmaceutical regimen to a human for a particular time period, the use of which requires intervention only for initiation and possibly terminiation of the regimen.

Yet still another object of the invention is to provide an osmotic device for dispensing separately two different drugs in known amounts per unit time.

Yet still another object of the invention is to provide an osmotic device that can deliver separately two different drugs and has an economic advantage for the user by keeping to a minimum the number of doses administered and reduces missed doses because of forgetfulness.

Other objects, features and advantages of the invention will be more apparent to those versed in the art from the following specification, taken in conjunction with the drawings and the accompanying claims.

BRIEF DESCRIPTION OF THE DRAWINGS

In the drawings, which are not drawn to scale, but are set forth to illustrate various embodiments of the invention, the Figures are as follows.

In the drawings and the specification, like parts in related figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
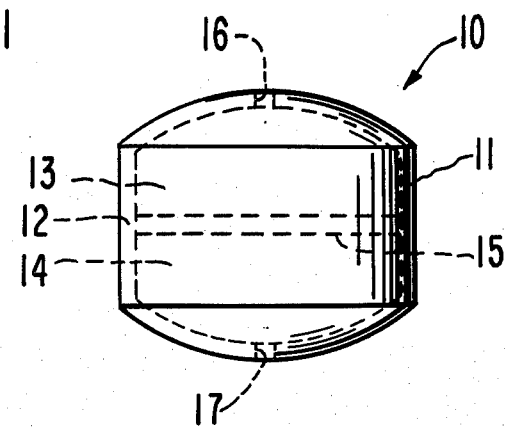
FIG. 1 is a view of an osmotic device designed and adapted for orally administering two beneficial drugs.
Figure 2:
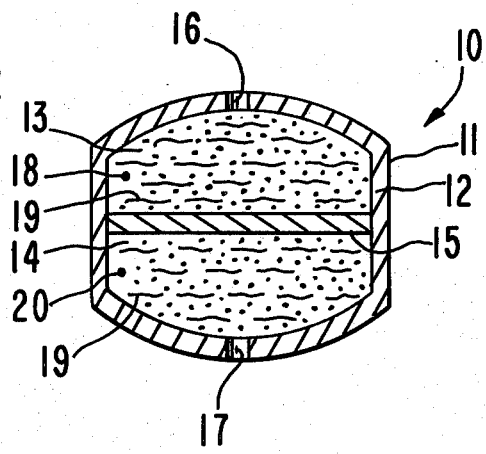
FIG. 2 is an opened view of the osmotic device of FIG. 1 for illustrating the structure of the osmotic device.
Figure 3:
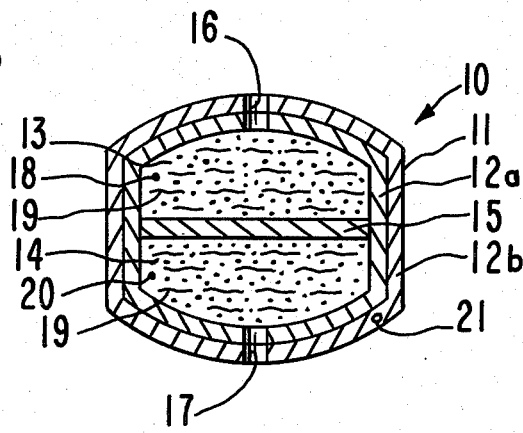
FIG. 3 is an opened view of the osmotic device of FIGS. 1 and 2 made with a laminated wall.

Turning now to the drawings in detail, which are an example of various osmotic delivery devices provided by the invention, and which example is not to be considered as limiting, one example of an osmotic device is indicated in FIGS. 1 to 3 and designated by the numeral 10. In FIG. 1, osmotic device 10 comprises a body 11 having a wall 12 that surrounds and forms an internal lumen divided into a first compartment 13, seen in dashed outline in FIG. 1, and in opened section in FIG. 2, and a second compartment 14 separated from adjoining compartment 13 by a partition 15. A first orifice 16 in wall 12 communicates with compartment 13 and the exterior of device 10, and a second orifice 17 communicates with compartment 14 and the exterior of device 10.

Compartment 13, as seen in FIG. 2, in one embodiment contains a beneficial drug 18, represented by dots, that is soluble in an external fluid and exhibits an osmotic pressure gradient across wall 12 against the fluid. Compartment 13 in another embodiment contains a drug 18 that has limited solubility in the external fluid and exhibits a limited solubility across wall 12 against the fluid. In this latter embodiment, drug 18 is mixed with an osmagent 19, indicated by wavy lines, that is soluble in the external fluid and exhibits an osmotic pressure gradient across wall 12 against the fluid. Compartment 14 contains a different drug 20 than drug 18. Drug 20 is soluble in the external fluid and exhibits an osmotic pressure gradient across wall 12, or drug 20 has limited solubility in the fluid and exhibits a limited pressure gradient across wall 12. Drug 20 in this latter physical chemical state is mixed with osmagent 19 that is soluble in the fluid and exhibits an osmotic pressure gradient across wall 12. Osmagent 19 can be the same or different in first compartment 13 and second compartment 14.

Wall 12 of osmotic device 10, as seen in FIGS. 1 and 2, comprises a semipermeable wall formed of a material that is permeable to the passage of an external fluid and it is essentially impermeable to the passage of drug 18, drug 20, and osmagent 19. Wall 12 is substantially inert, it maintains its physical and chemical integrity during the dispensing of the beneficial drugs, and it is non-toxic to animals including humans. Wall 12 of osmotic device 10, as seen in an embodiment in FIG. 3, comprises a laminate formed of a semipermeable lamina 12a in laminar arrangement with a microporous lamina 12b. Microporous lamina 12b consists of preformed microporores 21, or micropores formed in the environment of use. Microporous lamina 12b is inert and non-toxic. In FIG. 3, device 10 is manufactured in the embodiment illustrated with microporous lamina 12b facing the environment of use, and with semipermeable lamina 12a facing the lumen of device 10. In another embodiment, device 10 is manufactured with microporous lamina 12b positioned inside and with semipermeable lamina 12a positioned outside facing the environment of use. Both the semipermeable lamina and the microporous lamina can contain additional wall forming agents such as flux enhancers, flux reducers, plasticizers and the like.

The osmotic delivery system as seen in FIGS. 1 through 3 can be made into many embodiments including the presently preferred embodiments for oral use, that is, for releasing locally or systemically acting therapeutic medicaments in the gastrointestinal tract over a prolonged period of time. The oral system can have various conventional shapes and sizes such as round with a diameter of ⅛ inch to ½ inch, or it can be shaped like a capsule having a range of sizes from triple zero to zero, and from 1 to 8. In these manufactures system 10 can be adapted for administering drug to numerous animals, including warm blooded mammals, avians, reptiles and pisces.

While FIGS. 1 through 3 are illustrative of various delivery systems that can be made according to the invention, it is to be understood these systems are not to be considered as limiting, as the system can take a wide variety of shapes, sizes and designs adapted for delivering the drug to different biological environments of use. For example, the delivery system includes anal-rectal, artificial gland, blood system, buccal, cervical, dermal, ear, implant, intrauterine, nasal, subcutaneous, vaginal and the like.

DETAILED DESCRIPTION OF THE INVENTION

Figure 4:
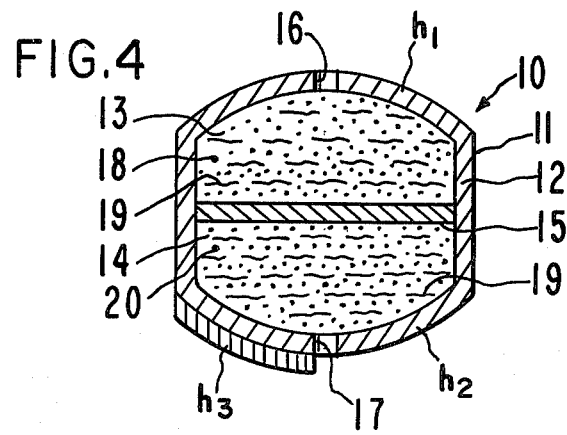
FIG. 4 is an opened view of the osmotic device of FIGS. 1 and 2 depicting an added lamina.

In accordance with the practice of this invention it has now been found an osmotic delivery system can be made for delivering at least two different drugs independently and simultaneously to a biological environment of use. The delivery system comprises the two compartments as seen in FIGS. 1 to 3 discussed above, with the drugs delivered independently from each compartment. The system described here is made with the same membrane composition and thickness on each compartment. The delivery equation for each osmotic compartment is given by equation 1.

$$\frac{dm}{dt} = \frac{KA\Delta\pi S_D}{h} \quad (1)$$

wherein K is the water permeability constant for the wall, A is the area of exposed surface of a compartment, $\Delta\pi$ is the difference between the osmotic pressure in a compartment compared with the external osmotic pressure, $S_D$ is the solubility of the drug in fluid that enters the compartment, and h is the thickness of the wall of the device. The ratio of release rates from compartment 1, the first compartment, to compartment 2, the second compartment, is given by equation 2.

$$\frac{\frac{dm}{dt}1}{\frac{dm}{dt}2} = \frac{\frac{K_1 A_1 \Delta\pi_1 S_{D1}}{h_1}}{\frac{K_2 A_2 \Delta\pi_2 S_{D2}}{h_2}} = \frac{A_1 \Delta\pi_1 S_{D1}}{A_2 \Delta\pi_2 S_{D2}} \quad (2)$$

wherein the K, A, $\pi$, and $S_D$ are as defined, and the wall on compartment 1 and compartment 2 are similar for homogenous walls, that is, the wall permeability $K_1=K_2$, and the wall thickness $h_1=h_2$. Equation 2 reveals that the ratio of delivery of one drug from one compartment to another drug from the other compartment is dependent only on the properties of the drugs, their associated osmagents, and surface areas of the compartments. The relative release rate from each compartment is modified or changed, by changing the composition in each compartment, and not the composition of the wall. Alternatively, the two compartments can be manufactured to have separate wall compositions and or thicknesses such that the two rates can be engineered independently of each other using also the membrane properties. Such a structure can be achieved by coating the total system with the same membrane and subsequently layering a separate laminate with thickness $h_3$ onto either compartment (1) or (2), as illustrated in FIG. 4, wherein $h_1$ is the thickness of the wall surrounding the first compartment, $h_2$ is the thickness of the wall at the second compartment, and $h_3$ is the thickness of the lamina added to the second compartment. Lamina h₂ can be formed of a different semipermeable material, a material impermeable to fluid, a material that bioerodes over time, and the like.

The materials forming the semipermeable wall of the delivery device are those that do not adversely affect the drug and the osmagent, an animal body, or other host, is permeable to an external fluid, such as water and biological fluid, while remaining essentially impermeable to drug, osmagents, and the like. The selectivity permeable materials forming wall 12 are insoluble in body fluids, they are nonerodible, or they can be made to bioerode after a predetermined period with bioerosion corresponding to the end of the drug release period. Typical materials for forming wall 12 include semipermeable materials known to the art as osmosis and reverse osmosis polymers. The semipermeable polymers include cellulose acylate, cellulose diacylate, cellulose triacylate, cellulose acetate, cellulose diacetate, cellulose triacetate, beta-glucan acetate, acetaldehyde dimethyl acetate, cellulose acetate ethyl carbamate, polyamide, polyurethane, sulfonated polystyrene, cellulose acetate phthalate, cellulose acetate methyl carbamate, cellulose acetate succinate, cellulose acetate dimethylaminoacetate, cellulose acetate chloroacetate, cellulose dipalmitate, cellulose dioctanoate, cellulose dicaprylate, cellulose dipentanlate, cellulose acetate valerate, cellulose acetate p-toluenesulfonate, cellulose acetate butyrate, ethylcellulose, selectively permeable polymers formed by the coprecipitation of a polycation and a polyanion as disclosed in U.S. Pat. Nos. 3,173,876; 3,276,586; 3,541,005; 3,541,006 and 3,546,142. Generally, semipermeable materials useful for forming wall 12 will have a fluid permeability of $10^{-5}$ to $10^{-1}$ (cc.mil/cm².hr.atm) expressed per atmosphere of hydrostatic or osmotic pressure across wall 12 at the temperature of use. Other suitable materials are known to the art in U.S. Pat. Nos. 3,845,770; 3,916,899; 4,036,228 and 4,111,202.

The microporous materials comprising microporous lamina 12b maintains their physical and chemical integrity during the period of time drug is released from system 10. The microporous materials comprising lamina 12b generally can be described as having a sponge-like appearance that provides a supporting structure for microscopic sized interconnected pores or voids. The materials can be isotropic wherein the structure is homogenous throughout a cross-sectional area, the materials can be anisotropic wherein the structure is nonhomogenous throughout a cross-sectional area, or the materials can have both cross-sectional areas. The materials are opened-celled, as the micropores are continuous or connected, with pores having an opening on both faces of the microporous lamina. The micropores are interconnected through tortuous paths of regular and irregular shapes including linear, curved, curved-linear, randomly oriented continuous pores, hindered connected pores, and other interconnected porous paths discernable by microporous examination.

Generally, the microporous lamina are characterized as having a reduced bulk density as compared to the bulk density of the corresponding non-porous microporous lamina. The morphological structure of the total microporous wall have a greater proportion of total surface area than the non-porous wall. The microporous wall can be further characterized by the pores size, the number of pores, the tortuosity of the microporous paths, and the porosity which relates to the size and the number of pores. Generally, material possessing from 5% to 95% pores, and having a pore size of from 10 angstroms to 100 microns can be used for making wall 12.

Materials useful for making the microporous lamina include polycarbonates comprised of linear polyesters of carbonic acid in which carbonate groups recur in the polymer chain, microporous materials prepared by the phosgenation of a dihydroxyl aromatic such as bisphenol, a microporous poly(vinylchloride), microporous polyamides such as polyhexamethylene adipamide, microporous modacrylic copolymers including those formed from poly(vinylchloride) and acrylonitrile, microporous styrene-acrylic and its copolymers, porous polysulfones characterized by diphenylene sulfone in a linear chain thereof, halogenated poly(vinylidene), polychloroethers, acetal polymers, polyesters prepared by esterification of a dicarboxylic acid or anhydride with an alkylene polyol, poly(alkylenesulfides), phenolics, polyesters, microporous polysaccharides having substituted anhydroglucose units exhibiting a decrease permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,601; 3,852,224; 3,852,388; and 3,853,601; in British Pat. No. 1,126,849; and In *Chem. Abst.* Vol. 71, 427F, 22573F, 1969.

Additional microporous materials for forming microporous lamina 12b include poly(urethane), cross-linked chain-extended poly(urethane), poly(imides), poly(benzimidazoles), collodion, regenerated proteins, semi-solid cross-linked poly(vinyl-pyrrolidone), microporous materials prepared by diffusion or multivalent cations into polyelectrolyte sols, microporous derivatives of poly(styrene) such as poly(sodium-styrene-sulfonate), poly(vinyl benzyl trimethyl-ammonium chloride), microporous cellulosic acylates and the like microporous polymers are known in U.S. Pat. Nos. 3,524,753; 3,565,259; 3,276,589; 3,541,055; 3,541,006; 3,546,142; 3,615,024; 3,646,178; and 3,852,224.

The pore-formers useful for forming the microporous lamina in the environment of use include solids and pore-forming liquids. The term pore-former as used herein also embraces micropath formers, and removal of the pore and/or pore-former leads to both embodiments. In the expression pore-forming liquids, the term for this invention generically embraces semi-solids and viscous fluids. The pore-formers can be inorganic or organic and the lamina forming polymer usually contains from 5 to 70% by weight of the pore-former, and more preferably about 20 to 50% by weight. The term pore-former for both solids and liquids include substances that can be dissolved, extracted or leached from the precursor microporous wall by fluid present in the environment of use to form operable, open-celled type microporous lamina. The pore-forming solids have a size of about 0.1 to 200 microns and they include alkali metal salts such as lithium carbonate, sodium chloride, sodium bromide, potassium chloride, potassium sulfate, potassium phosphate, sodium acetate, sodium citrate, and the like. Organic compounds such as saccharides including the sugars sucrose, glucose, fructose, mannitol, mannose, galactose, sorbitol and the like. They can be polymers soluble in the environment of use such as Carbowaxes ®, Carbopol ®, and the like. The pore-formers embrace diols, polyols, polyhydric alcohols, polyalkylene glycols, polyglycols, poly($\alpha$-$\omega$)-alkylenediols, and the like. The pore-formers are non-toxic and on their removal from lamina 12b, channels and pores are formed through the lamina that fill with fluid present in the environment of use.

The partition between the first and second compartments is formed of a semipermeable, microporous, or impermeable polymer, which partition is impermeable to the passage of drug and osmagents. The impermeable polymer additionally is impermeable to the passage of fluid. The materials used for forming semipermeable and microporous partition are the above materials. Materials used for forming impermeable partitions include high density polyethylene and polypropylene, polyethylene terephthalate, aluminum foil coated with polyethylene, inert organic and inorganic materials, and the like. The partition can be formed of composites such as inorganic material added to a polymer, for example calcium phosphate added to cellulose acetate to form an inactive partition. In addition, the partition materials can be granulated such that it is pressed onto the first compartment, then the second compartment is pressed onto the partition using a standard layer tablet press. Generally, the partition 15 will have a thickness of about 2 to 10 mils and will function to maintain the integrity of the first and second compartments.

The expression orifice as used herein comprises means and methods suitable for releasing the drug from each compartment. The orifice will pass through the semipermeable wall, or through the semipermeable-microporous laminated wall for communicating each compartment with the exterior of the device. The expression includes passageway, or bore through wall formed by mechanical procedures or by eroding an erodible element, such as a gelatin plug in the environment of use. Generally, the orifice will have a diameter of 1 mil to 15 mils in the wall or laminate. A detailed description of osmotic orifices and the maximum and minimum dimensions for an orifice are disclosed in U.S. Pat. Nos. 3,845,770 and 3,916,899.

The osmagents, or osmotically effective compounds that can be used in the first compartment or in the second compartment include organic and inorganic compounds or solutes that exhibit an osmotic pressure gradient across the semipermeable wall against an external fluid. Osmagents, or osmotically effective compounds include magnesium sulfate, magnesium chloride, sodium chloride, lithium chloride, potassium sulfate, potassium acid phosphate, mannitol, urea, sucrose, and the like. Osmagents are known to the art in U.S. Pat. Nos. 3,854,770; 4,077,407; and 4,235,236.

The term drug as used in the specification and the accompanying claims includes physiologically or pharmacologically active substances that produce a localized or systemic effect or effects in animals, avians, pisces and reptiles. The active drug that can be delivered includes inorganic and organic compounds without limitation, those materials that act on the central nervous system such as hypnotics, sedatives, psychic energizers, tranquilizers, anticonvulsants, muscle relaxants, antiparkinson agents, analgesics, anti-inflammatory, local anesthetics, muscle contractants, anti-microbials, anti-malarials, hormonal agents, contraceptives, sympathomimetics, diuretics, anti-parasites, neoplastics, hypoglycemics, nutritional agents, ophthalmic, electrolytes, and the like. The drug housed and delivered from each compartment in a presently preferred embodiment embraces a different drug in the first compartment and in the second compartment respectively as represented by the following: anti-inflammatory and anti-pyretic, anti-inflammatory and analgesic, bronchodilator and vasodilator, beta-blocker and diuretic, beta-blocker and beta-blocker, beta-blocker and vasodilator, beta-agonist and muscle relaxant, beta-adrenergic agonist and histamine receptor antagonist, anti-histamine and decongestant, beta-adrenergic stimulator and muscle relaxant, anti-hypertensive and diuretic, analgesic and analgesic, antisposmatic and anticholenergic, tranquilizer and anticholenergic, anticholenergic and histamine receptor antagonist, and the like.

Exemplary drugs that can be in the first compartment and the second compartment include prenalterol in the first compartment and hydralazine in the second compartment as used in chronic congestive heart failure in short and long term therapy, propranolol in the first compartment and hydralazine in the second compartment for the management of hypertension, acetophenetidin in one compartment and aspirin in the other compartment for analgesic and anti-inflammatory therapy, phenacetin in one compartment and ethoxyacetanilide in the other compartment for antipyretic and analgesic therapy, magnesium trisilicate in one compartment and aspirin in the other compartment as an analgesic antacid therapy, cyptenamine tannate in one compartment and methylclothiazide in the other compartment for treating hypertension, meprobamate in one compartment and pentaerythritol tetranitrate used as prophylaxis in the management of angina pectoris, and in the first and second compartment theophylline and ephedrine for treating ambulatory asthmatics, theophylline and albuterol, ketolifen and theophylline, spironolactone and hydrochlorothiazide, chlorothalidone and spironolactone, and the like. The amount of drug in each compartment generally is from 0.05 ng to 1000 mg, with different devices having individual compartments containing 1 mg, 5 mg, 100 mg, 250 mg, and the like. The beneficial drugs are known to the art in *Pharmaceutical Sciences,* by Remington, 14th Ed., 1970 published by Mack Publishing Co., Easton, PA; and in *American Drug Index,* 1976, published by J. B. Lippincott Co., Philadelphia, PA.

The drug present in the compartments of the device can be in various forms, such as uncharged molecules, molecular complexes, pro-drug, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines, or organic cations, for example quaternary ammonium salts can be used. Derivatives of drugs such as esters, ethers and amides, which have solubility characteristics suitable for use herein can be used. The expression drug formulation as used herein generically includes the drug, or the drug in the various forms, in either embodiment mixed with a non-toxic osmagent in the first or in the second compartment. The drug can be in the compartment as a suspension, dispersion, paste, cream, particle, granule, emulsion, powder, and the like.

The osmotic device of the invention is manufactured by standard techniques. For example, in one manufacture, a drug and optionally an osmagent and other ingredients that may be housed in one compartment are mixed into a solid, semi-solid, moist, or pressed state by conventional methods such as ballmilling, calendering, stirring or roll-milling, and then pressed into a preselected shape. A partition is formed by molding, spraying, pressing, or dipping one surface of the pressed shape into the partition forming material. The second compartment is formed by pressing a drug, or optionally a drug and an osmagent into a preselected shape that corresponds to the above formed shape, and then intimately attaching it to the partition, or a drug and an osmagent can be pressed directly onto the partition. Finally, the two compartments are surrounded with a semipermeable wall, or they are surrounded by a laminated wall. Optionally, system 10 can be manufactured by first fabricating one compartment by pressing in a standard tableting machine a drug to form a predetermined shaped compartment which is then surrounded by a wall forming material to form a closed compartment. Next, the other compartment is formed by pressing drug to first compartment. Finally, the two adjacent compartments are surrounded with a wall formed of a semipermeable material, and a passageway is drilled through the wall into each compartment to form system 10 with two distinct compartments and two distinct orifices for dispensing two drugs from system 10.

The compartments, as described immediately above can be joined by methods well-known to the art, or they can be integrally formed as illustrated in the above figures. One operable method for joining the compartments consists in applying a dash or thin layer of a non-toxic adhesive to the joinable surfaces immediately preceeding their alignment into a working structure. Adhesives suitable for the present purpose include semipermeable silicon glue, cellulose nitrate, cellulose acetate, vinyl acetate and vinyl chloride adhesives, acrylic resins, aldehyde resins, water soluble gums, aqueous dispersions of paraffins, monomeric esters of α-cyanoacrylic acid, ureas, and the like. These adhesives are disclosed to the art in U.S. Pat. Nos. 3,547,771; 3,552,994; 3,598,781; 3,627,559; 3,627,609; 3,755,044; and 3,759,264; in West Germany Pat. No. DT2,009,968; and in British Pat. No. 577,735. The compartments also can be joined by other methods including heat sealing, pressing, consecutively casting the compartments in a dual cavity mold, overlaying, and the like.

The walls, lamina and partition forming the system can be joined by various techniques such as high frequency electronic sealing that provides clean edges and firmly formed walls, lamina and partitions, and, a presently preferred technique that can be used is the air suspension procedure. This procedure consists in suspending and tumbling the drug or osmagent in a current of air and a wall forming, or lamina forming, composition until the wall or lamina is applied to the drug. The air suspension procedure is well-suited for independently forming the walls and lamina. The air suspension procedure is described in U.S. Pat. No. 2,799,241; in *J. Am. Pharm. Assoc.*, Vol. 48, pages 451 to 459, 1959; and ibid., Vol. 49, pages 82 to 84, 1960. Other wall and laminating techniques such as pan coating can be used in which the materials are deposited by successive spraying of the polymer solution on the drug accompanied by tumbling in a rotating pan. Other standard manufacturing procedures are described in *Modern Plastics Encyclopedia*, Vol. 46, pages 62 to 70, 1969; and in *Pharmaceutical Sciences*, by Remington, 14th Ed., pages 1626 to 1678, 1970, published by Mack Publishing Company, Easton, Pa.

The microporous lamina, in optional manufacturing embodiments, can be manufactured with microporous wall forming polymers that are commercially available, or they can be made by art known methods. The microporous materials can be made and then manufactured into a device by etched nuclear tracking, by cooling a solution of flowable polymer below its freezing poing whereby solvent evaporates from the solution in the form of crystals dispersed in the polymer, and then curing the polymer followed by removing the solvent crystals, by cold or hot stretching of a polymer at low or high temperatures until pores are formed, by leaching from a polymer soluble pore forming component by use of an appropriate solvent, and by dissolving or leaching a pore former from the wall of a device in operation in the environment of use. Processes for preparing microporous materials are described in *Synthetic Polymer Membranes*, by R. E. Kesting, Chapters 4 and 5, 1971, published by McGraw Hill, Inc; *Chemical Reviews, Ultrafiltration*, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,224; and 3,849,528.

Generally, the semipermeable wall will have a thickness of 2 to 20 mils, with a presently preferred thickness of 4 to 12 mils. The partition between the compartment generally will have a thickness of 1 mil to 7 mils, with a presently preferred thickness of 2 to 5 mils. In laminated walls, the lamina will have a thickness of 2 to 10 mils with a presently preferred thickness of 2 to 5 mils. Of course, thinner and thicker walls, lamina and partitions for use with numerous drugs and osmagents are within the scope of the invention.

Exemplary solvents suitable for manufacturing the wall and the lamina include inert inorganic and organic solvents that do not adversely harm the wall and lamina materials, and the final system. The solvents broadly include members selected from the group consisting of aqueous solvents, alcohols, ketones, esters, ethers, aliphatic hydrocarbons, halogenated solvents, cycloaliphatic aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclo-hexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and mixtures thereof.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic delivery device for the controlled and continuous delivery of the two beneficial drugs hydralazine and metoprolol to a biological environment of use is manufactured as follows: first, a reservoir forming composition for housing in one compartment is compounded from 50 mg of hydralazine hydrochloride, 208 mg of mannitol, 8 mg of hydroxypropylmethylcellulose and 8 mg of stearic acid by mixing the hydralazine hydrochloride and the mannitol and then passing the mixture through a 40-mesh screen, next, the hydroxypropyl methylcellulose is dissolved in a 70/30 (w/w/%) ethanol-water solution and the hydralazine-mannitol mixture is added to the wet hydroxypropyl methylcellulose and all the ingredients blended for 10 minutes. Next, the blend is passed through a 10-mesh screen and spread on a tray and dried in an oven at 50° C. for 18-24 hours. The dried blend is passed through a 20-mesh screen, placed in a mixer, and the stearic acid added to the blend and the mixing continued for 10 minutes.

A second reservoir forming composition comprising 190 mg of metoprolol fumarate, 10 mg of polyvinyl pyrrolidone, and 3 mg of magnesium stearate is made by first passing the metoprolol fumarate through a 40-mesh screen, next, the polyvinyl pyrrolidone is dissolved in a 70/30 (w/w/%) ethanol-water solution, the metoprolol fumarate is placed in a mixer and the wet polyvinyl pyrrolidone added thereto. The ingredients are mixed for 10 minutes, passed through a 10-mesh screen and dried in an oven at 50° C. for 24 hours. Next, the dried blend is passed through a 20-mesh screen, placed in a mixer and the magnesium stearate added and the ingredients again blended to yield the reservoir composition.

A compartment containing 274 mg of the hydralazine hydrochloride drug formulation as described above is prepared by placing the formulation in a 7/16 inch convex round die and the turret of the compression machine turned until the load reaches the compression point with the formulation compressed into the shape of the die. The turret is reversed back to the loading position and 100 mg of solid cellulose acetate is spread over the compressed hydralazine formulation to form a partition. Next, another compartment consisting essentially of 200 mg of the metoprolol fumarate formulation as described above, is prepared by adding the formulation to the die in contact with the partition, and the formulation pressed against the partition. The two united compartments were then coated in a suspension-coating machine with a wall of semipermeable cellulose acetate from a wall forming composition comprising 85% cellulose acetate having an acetyl composition of 36%, and 15% hydroxypropyl methylcellulose dissolved in an 80 to 20 parts by weight of a methylene chloride-methanol solvent. The two compartments are coated with the cellulose acetate solution to form a semipermeable wall having a thickness of 6 mils. The coated compartments are dried in a forced air oven at 50° C. for one week, and an orifice is laser drilled through the wall into one compartment, and then an orifice is drilled through the wall communicating with the other compartment. The orifices have a diameter of 10 mils for delivering each drug from the device. The osmotic system has a release rate of 2 mg/hr for hydralazine hydrochloride and 13 mg/hr for metoprolol fumarate.

EXAMPLE 2

An osmotic therapeutic system manufactured in the form of an oral, osmotic device for delivering two drugs to the gastrointestional tract is manufactured as follows: first, 275 mg of a drug formulation consisting essentially of 18.2% hydrazaline hydrochloride, 75.9% mannitol, 2.9% hydroxypropylmethyl cellulose and 3% stearic acid is pressed into a solid mass in a commercially available Manesty tableting machine to a Stoke's hardness of 8 kp. Next, a drop of liquid cellulose acetate is spread onto one surface of the pressed formulation. Then, 203 mg of a drug formulation consisting essentially of 93.5% metoprolol fumarate, 5% polyvinyl pyrrolidone and 1.5% magnesium stearate is placed in the Manesty press on top of the cellulose acetate that forms a partition separating the two different drug formulations. Next, the formulation is pressed to a Stoke's hardness of 8 kp. The two united drug formulations are then coated in an air suspension machine, first with an interior lamina consisting of 65% cellulose acetate having an acetyl content of 36% and 35% hydroxypropyl methylcellulose to a thickness of 3.9 mil from a methylene chloride-methanol solvent, and then with an exterior lamina consisting essentially of 85% cellulose acetate and 15% hydroxypropyl methyl cellulose forming a 1 mil thick lamina from a methylene chloride-methanol solvent. The osmotic device is dried in a forced oven at 50° C. for 120 hours and a 10 mil osmotic orifice is drilled through the laminate facing the hydrazaline compartment and another 10 mil osmotic orifice is drilled through the laminate facing the metoprol compartment.

EXAMPLE 3

The procedures of Examples 1 and 2 are followed for producing delivery devices housing separately in the compartments salbutamol and theophylline, chlordiazepoxide hydrochloride and clidinium bromide, acetaminophen and oxycodone, pindolol and thiazide, cimetidine and salbutamol, burimamide and pirenzepine, cimetidine and propantheline, cimetidine and isopropamide, and the like.

EXAMPLE 4

Figure 5:
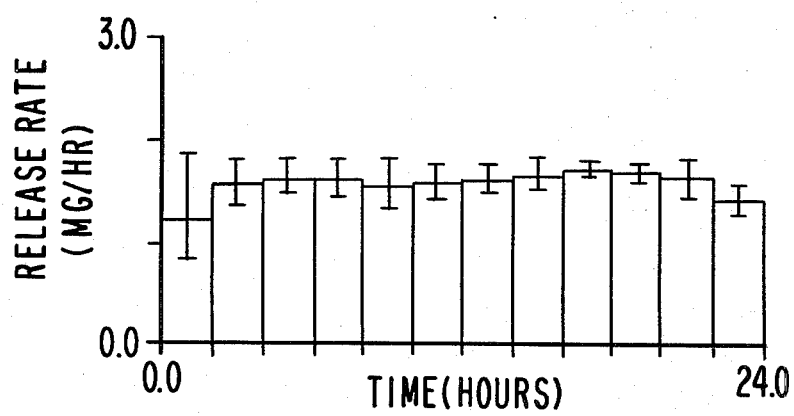
FIG. 5 is a graph illustrating the release rate of a drug from the first compartment.
Figure 6:
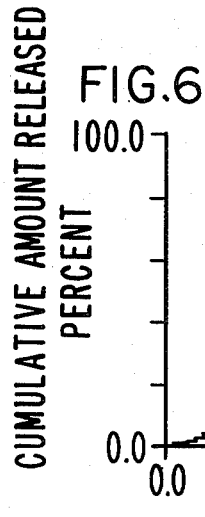
FIG. 6 is a graph illustrating the cumulative amount of the drug of FIG. 5 released from the first compartment.
Figure 7:
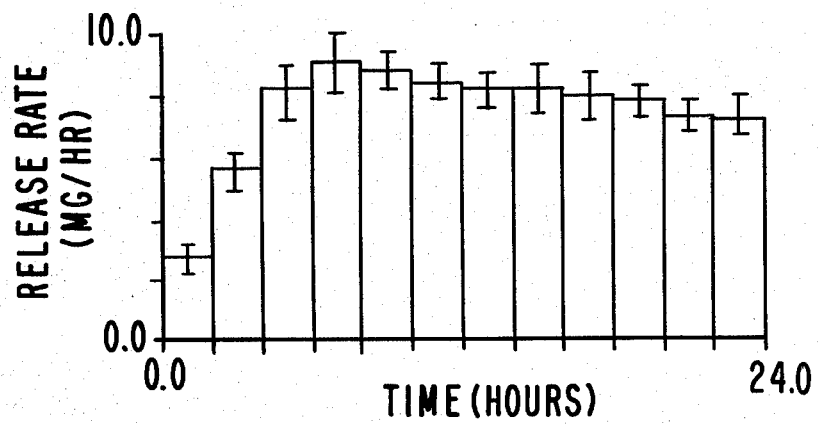
FIG. 7 is a graph illustrating the release rate of a drug from the second compartment.
Figure 8:
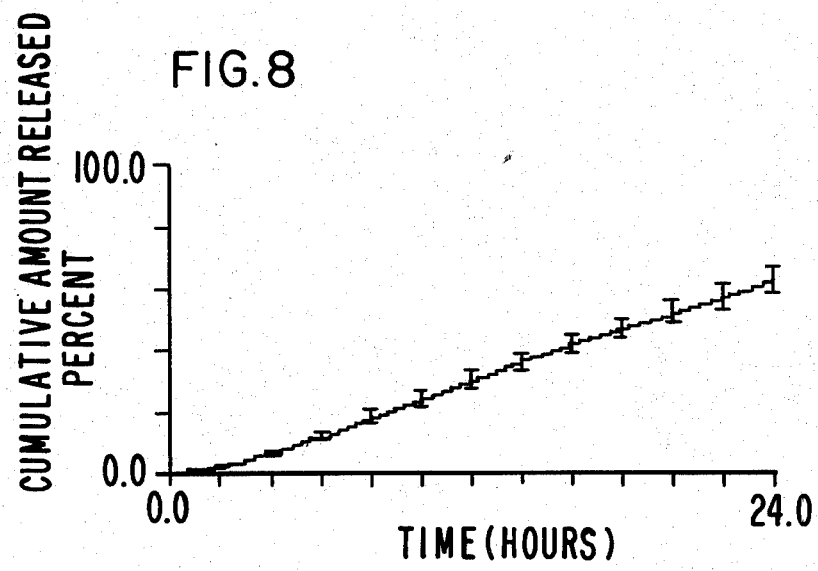
FIG. 8 is a graph illustrating the cumulative amount of the drug of FIG. 7 released from the second compartment.

The procedures of Example 1 and 2 are followed for producing an oral osmotic delivery device comprising in the first compartment 7.3% (total core weight basis) hydralazine hydrochloride, 30.6% mannitol, and in the second compartment 42.6% oxprenolol sebacinate and 14.1% sodium bicarbonate. The partition between the first compartment and the second compartment consists essentially of 5.4% hydroxypropyl cellulose, and the wall of the device consists of 40% cellulose acetate having an acetyl content of 32%, cellulose acetate having an acetyl content of 39.8% and 18% hydroxypropyl methylcellulose. Accompanying FIG. 5 depicts the release rate in mg/hr of hydralazine hydrochloride from this device, FIG. 6 depicts the cumulative amount of hydralazine hydrochloride released over time, FIG. 7 depicts the release rate in mg/hr of oxprenolol sebacinate and FIG. 8 depicts the cumulative amount released over time from the device.

The novel osmotic systems of this invention are means for the obtainment of precise release rates in theenvironment of use while simultaneously maintaining the integrity and character of the osmotic system and the drugs. While there has been described and pointed out features of the invention as applied to presently preferred embodiments, those skilled in the art will appreciate that various modifications, changes, additions and omissions in the system illustrated and described can be made without departing from the spirit of the invention.

We claim:

1. An osmotic therapeutic device for the controlled delivery of beneficial drugs to a biological environment, the device consisting essentially of:
   (a) a wall formed of a semipermeable material permeable to the passage of an external fluid present in the environment and substantially impermeable to the passage of drug, the semipermeable wall surrounding and forming;
   (b) a first compartment containing a drug formulation that exhibits an osmotic pressure gradient across the semipermeable wall against an external fluid;
   (c) a second compartment containing a drug formulation that exhibits an osmotic pressure gradient across the semipermeable wall against an external fluid;
   (d) a partition positioned between the first and second compartments, which partition is formed of a material selected from the group consisting essentially of semipermeable, microporous and impermeable materials;
   (e) a first orifice in the wall communicating with the first compartment and the exterior of the device for delivering drug formulation from the first compartment to the environment over a prolonged period of time; and,
   (f) a second orifice in the wall communicating with the second compartment and the exterior of the device for delivering drug formulation from the second compartment to the environment over a prolonged period of time.

2. The osmotic therapeutic device for the controlled delivery of beneficial drugs according to claim 1, wherein when the device is in operation in the environment of use, fluid from the environment is imbibed through the wall into (1) the first compartment in a tendency towards osmotic equilibrium at a rate determined by the permeability of the wall and the osmotic pressure gradient across the wall, thereby forming a solution containing drug that is delivered through the first orifice from the device at a controlled rate over a prolonged period of time, and into (2) the second compartment in a tendency towards osmotic equilibrium at a rate determined by the permeability of the wall and the osmotic pressure gradient across the wall, thereby forming a solution containing drug that is delivered through the second orifice from the device at a controlled rate over a prolonged period of time.

3. The osmotic therapeutic device for the controlled delivery of beneficial drugs according to claim 1, wherein the drug formulation in the first compartment comprises a dosage unit amount of drug and an osmagent.

4. The osmotic therapeutic device for the controlled delivery of beneficial drugs according to claim 1, wherein the drug formulation in the second compartment comprises a dosage unit amount of drug and an osmagent.

5. The osmotic therapeutic device for the controlled delivery of beneficial drugs according to claim 1, wherein the first and second compartments contain different drugs.

6. The osmotic therapeutic device for the controlled delivery of beneficial drugs according to claim 1, wherein the device is adapted for oral administration for delivering drugs to the gastrointestional tract.

7. The osmotic therapeutic device for the controlled delivery of beneficial drugs according to claim 1, wherein the drug in the first compartment is a bronchodilator and the drug in the second compartment is a vasodilator.

8. The osmotic therapeutic device for the controlled delivery of beneficial drugs according to claim 1, wherein the drug in the first compartment is a beta-blocker and the drug in the second compartment is a diuretic.

9. The osmotic therapeutic device for the controlled delivery of beneficial drugs according to claim 1, wherein the drug in the first compartment is a beta-blocker and the drug in the second compartment is a vasodilator.

10. The osmotic therapeutic device for the controlled delivery of beneficial drugs according to claim 1 wherein the drug in the first compartment is a beta-agonist and the drug in the second compartment is a muscle relaxant.

11. The osmotic therapeutic device for the controlled delivery of beneficial drugs according to claim 1, wherein the drug in the first compartment is a beta-adrenergic agonist and the drug in the second compartment is a histamine receptor antagonist.

12. The osmotic therapeutic device for the controlled delivery of beneficial drugs according to claim 1, wherein the drug in the first compartment is a beta-blocker and the drug in the second compartment is an anti-hypertensive.

13. The osmotic therapeutic device for the controlled delivery of beneficial drugs according to claim 1, wherein the drug in the first compartment is a beta-adrenergic stimulator and the drug in the second compartment is a muscle relaxant.

14. The osmotic therapeutic device for the controlled delivery of beneficial drugs according to claim 1, wherein the drug in the first compartment is an antihypertensive and the drug in the second compartment is a diuretic.

15. The osmotic therapeutic device for the controlled delivery of beneficial drugs according to claim 1, wherein the drug in the first compartment is an antispasmodic and the drug in the second compartment is an anticholenergic.

16. The osmotic therapeutic device for the controlled delivery of beneficial drugs according to claim 1, wherein the drug in the first compartment is an anticholinergic and the drug in the second compartment is a histamine receptor antagonist.

17. The osmotic therapeutic device for the controlled delivery of beneficial drugs according to claim 1, wherein the drug in the first compartment is a tranquilizer and the drug in the second compartment is an anticholinergic.

18. The osmotic therapeutic device for the controlled delivery of beneficial drugs according to claim 1, wherein the wall surrounding the first compartment is formed of a different material and thickness than the wall surrounding the second compartment.

19. An osmotic therapeutic device for the controlled delivery of beneficial drugs to a biological environment, the device consisting essentially of:

(a) a laminated wall formed of a semipermeable lamina in laminar arrangement with a microporous lamina, the laminated wall surrounding and forming;
(b) a first compartment containing a drug formulation that exhibits an osmotic pressure gradient across the laminated wall against an external fluid;
(c) a second compartment containing a drug formulation that exhibits an osmotic pressure gradient across the laminated wall against an external fluid;
(d) a partition positioned between the first compartment and the second compartment, which partition is formed of a material selected from the group consisting essentially of semipermeable, microporous, and impermeable materials;
(e) a first orifice in the laminated wall communicating with the first compartment and the exterior of the device for delivering drug formulation from the first compartment to the environment over a prolonged period of time; and,
(f) a second orifice in the laminated wall communicating with the second compartment and the exterior of the device for delivering drug formulation from the second compartment to the environment over a prolonged period of time.

20. The osmotic therapeutic device for the controlled delivery of beneficial drugs according to claim 19, wherein when the device is in operation in the environment of use, fluid from the environment is imbibed through the laminated wall into (1) the first compartment in a tendency towards osmotic equilibrium at a rate determined by the permeability of the wall and the osmotic pressure gradient across the wall, thereby forming a solution containing drug that is delivered through the first orifice from the device at a controlled rate over a prolonged period of time, and into (2) the second compartment in a tendency towards osmotic equilibrium at a rate determined by the permeability of the wall and the osmotic pressure gradient across the wall, thereby forming a solution containing drug that is delivered through the second orifice from the device at a controlled rate over a prolonged period of time.

21. The osmotic therapeutic device for the controlled delivery of beneficial drugs according to claim 19 wherein the drug formulation in the first compartment comprises a dosage unit amount of drug and an osmagent.

22. The osmotic therapeutic device for the controlled delivery of beneficial drugs according to claim 19 wherein the drug formulation in the second compartment comprises a dosage unit amount of drug and an osmagent.

23. The osmotic therapeutic device for the controlled delivery of beneficial drugs according to claim 19 wherein the first and second compartments contain different drugs.

24. The osmotic therapeutic device for the controlled delivery of beneficial drugs according to claim 19 wherein the device is adapted for oral administration for delivering drugs to the gastrointestional tract.

25. The osmotic therapeutic device for the controlled delivery of beneficial drugs according to claim 19 wherein the semipermeable lamina faces the compartments and the microporous lamina faces the environment.

26. The osmotic therapeutic device for the controlled delivery of beneficial drugs according to claim 19 wherein the microporous lamina faces the compartments and the semipermeable lamina faces the environment.

27. The osmotic therapeutic device for the controlled delivery of beneficial drugs according to claim 19, wherein the drug in the first compartment is a bronchodilator and the drug in the second compartment is a vasodilator.

28. The osmotic therapeutic device for the controlled delivery of beneficial drugs according to claim 19, wherein the drug in the first compartment is a beta-blocker and the drug in the second compartment is a diuretic.

29. The osmotic therapeutic device for the controlled delivery of beneficial drugs according to claim 19, wherein the drug in the first compartment is a beta-blocker and the drug in the second compartment is a vasodilator.

30. The osmotic therapeutic device for the controlled delivery of the beneficial drugs according to claim 19, wherein the drug in the first compartment is a beta-agonist and the drug in the second compartment is a muscle relaxant.

31. The osmotic therapeutic device for the controlled delivery of beneficial drugs according to claim 19, wherein the drug in the first compartment is a beta-adrenergic agonist and the drug in the second compartment is a histamine receptor antagonist.

32. The osmotic therapeutic device for the controlled delivery of beneficial drugs according to claim 19, wherein the drug in the first compartment is a beta-blocker and the drug in the second compartment is an anti-hypertensive.

33. The osmotic therapeutic device for the controlled delivery of beneficial drugs according to claim 19, wherein the drug in the first compartment is a beta-adrenergic stimulator and the drug in the second compartment is a muscle relaxant.

34. The osmotic therapeutic device for the controlled delivery of beneficial drugs according to claim 19, wherein the drug in the first compartment is an antihypertensive and the drug in the second compartment is a diuretic.

35. The osmotic therapeutic device for the controlled delivery of beneficial drugs according to claim 19 wherein the drug in the first compartment is an antispasmotic and the drug in the second compartment is an anticholenergic.

36. The osmotic therapeutic device for the controlled delivery of beneficial drugs according to claim 19, wherein the drug in the first compartment is an anticholinergic and the drug in the second compartment is a histamine receptor antagonist.

37. The osmotic therapeutic device for the controlled delivery of beneficial drug according to claim 19, wherein the drug in the first compartment is a tranquilizer and the drug in the second compartment is an anticholinergic.

38. The osmotic therapeutic device for the controlled delivery of beneficial drugs according to claim 19 wherein the wall surrounding the first compartment is formed of a different material and thickness than the wall surrounding the second compartment.

* * * * *